United States Patent [19]

Tarman

[11] 4,431,509
[45] Feb. 14, 1984

[54] HYDROCARBON PRODUCTION BY FREE FALL COUNTERCURRENT FLOW HYDROCONVERSION

[75] Inventor: Paul B. Tarman, Elmhurst, Ill.

[73] Assignee: Institute of Gas Technology, Chicago, Ill.

[21] Appl. No.: 386,721

[22] Filed: Jun. 9, 1982

[51] Int. Cl.³ .................. C10G 1/06; C10B 53/06; C10J 3/46
[52] U.S. Cl. .................. 208/8 R; 208/11 R; 48/197 R; 48/210
[58] Field of Search ............ 208/8 R, 11 R; 48/197 R, 210; 585/240

[56] References Cited

U.S. PATENT DOCUMENTS

| | | | |
|---|---|---|---|
| 3,088,816 | 5/1963 | Huntington | 48/197 R |
| 3,106,521 | 10/1963 | Huntington | 208/11 R |
| 3,107,985 | 10/1963 | Huntington | 48/197 R |
| 3,247,092 | 4/1966 | Huntington | 208/8 R |
| 3,421,868 | 1/1969 | Feldman | 48/197 R |
| 3,565,784 | 2/1971 | Schlinger et al. | 208/11 R |
| 3,891,403 | 6/1975 | Weil et al. | 48/197 R |
| 3,922,215 | 11/1975 | Linden et al. | 208/11 R |
| 4,003,820 | 1/1977 | Pelofsky et al. | 208/8 R |
| 4,003,821 | 1/1977 | Weil et al. | 208/11 R |
| 4,012,311 | 3/1977 | Greene | 208/8 R |
| 4,048,053 | 9/1977 | Greene | 208/8 R |
| 4,075,083 | 2/1978 | Putman | 208/11 R |

Primary Examiner—Delbert E. Gantz
Assistant Examiner—Glenn A. Caldarola
Attorney, Agent, or Firm—Thomas W. Speckman

[57] ABSTRACT

A process and apparatus for production of liquid and gaseous hydrocarbon products from solid organic carbonaceous materials by reacting free falling solids with a countercurrent hydrogen-containing gas stream. The process is conducted with a lean solids phase which provides good process control and uniform flow of solids even in the presence of condensation and refluxing of liquids on the solid particles. Oil shales of the Eocene period having Modified Fischer Assays of less than about 9 gallons of oil per ton and representing less than half the organic carbon present in the oil shale are particularly well suited for the process of this invention. A reactor particularly suited for conducting reactions between free falling solids and countercurrent flowing gas streams is disclosed together with preferred methods for introduction of solid feeds to the top of the reactor including distribution baffles and fluidized bed feed distribution systems.

17 Claims, 2 Drawing Figures

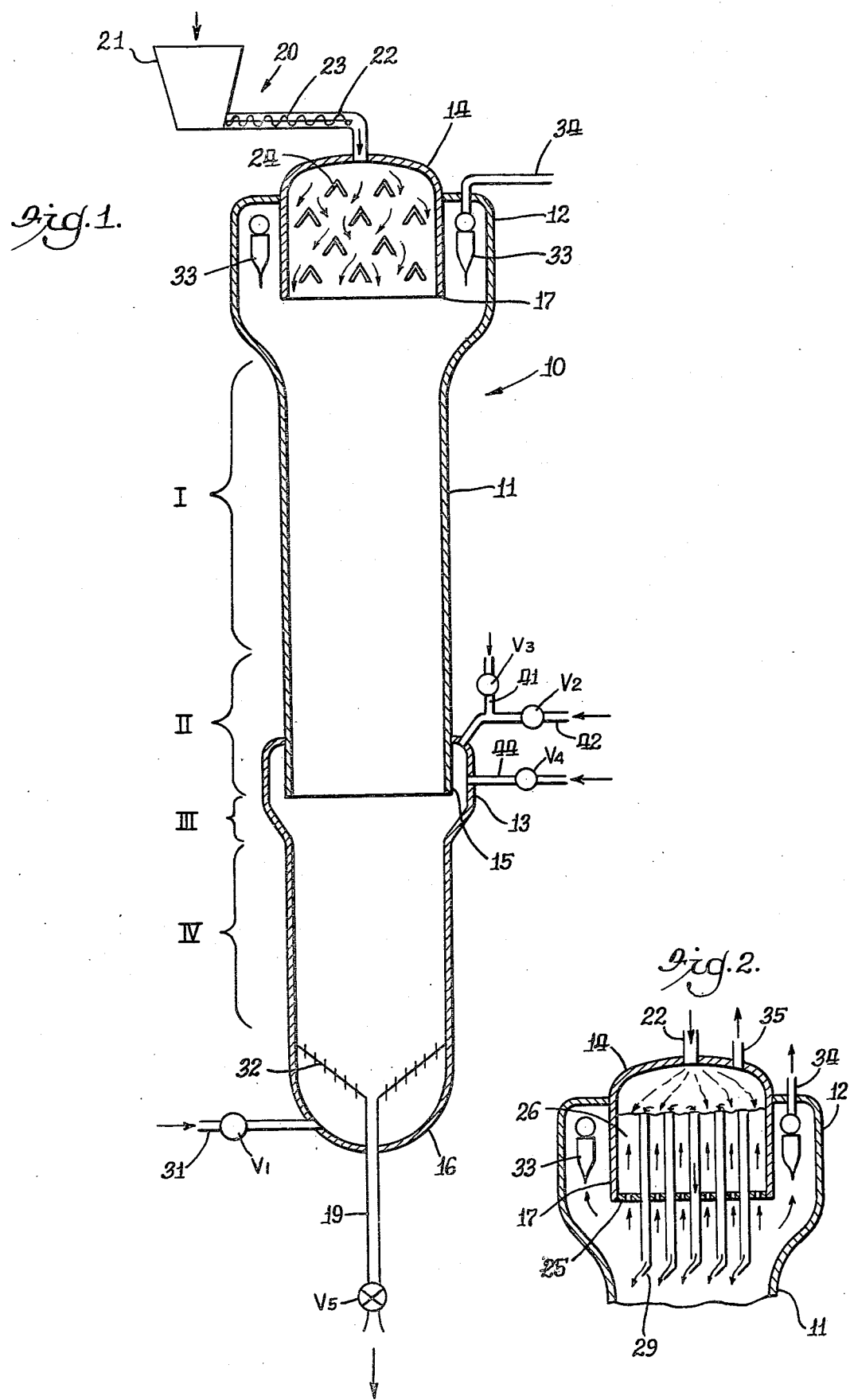

HYDROCARBON PRODUCTION BY FREE FALL COUNTERCURRENT FLOW HYDROCONVERSION

BACKGROUND OF THE INVENTION

1. Field of the Invention

This invention relates to production of principally hydrocarbon liquid and low molecular weight gaseous hydrocarbon products from organic carbonaceous solids by countercurrent flow of hydrogen-containing gas with the solids through a reactor, the solids passing sequentially through a preheat and pretreatment zone, a reaction zone and a hydrogen-containing gas preheat zone. Hydrocarbon liquid and low molecular weight gaseous hydrocarbon products, particularly useful as fuels, may be produced from organic carbonaceous materials such as oil shale, coal, peat and biomass.

2. Description of the Prior Art

The worldwide energy shortage has encouraged consideration and improvement of various processes for production of hydrocarbon fuels which do not involve petroleum products. Non-petroleum materials such as oil shale, coal, peat and biomass represent a large potential energy resource.

The production of hydrocarbon fuels by hydroconversion of oil shale has been known. For example, U.S. Pat. No. 4,003,821 teaches production of liquid hydrocarbons from oil shale by passing a hydrogen-rich gas stream countercurrent to a packed moving bed or fluidized bed of oil shale particles. The '821 patent teaches use of hydrogen sufficient to meet chemical requirements and the desirability of a sufficient excess of hydrogen to convert all of the hydrocarbons and carbon monoxide produced to methane. U.S. Pat. No. 3,922,215 teaches production of liquid hydrocarbons from oil shale by passing a hydrogen-rich gas stream in contact with oil shale particles in a moving bed. The '215 patent teaches the preferability of passing the hydrogen-rich gas stream in cocurrent relation with the oil shale particles to avoid condensation of hydroretorted liquids. The problems of condensation of liquids on the solid particles has been recognized by the prior art, for example, in U.S. Pat. No. 3,619,405. U.S. Pat. Nos. 3,891,403 and 3,929,615 teach production of high methane content gas from oil shale by hydrogasification.

Several patents teach various methods of retorting hydrocarbonaceous solids utilizing moving solids beds wherein gas passes countercurrently, such as U.S. Pat. Nos. 3,841,992; 3,619,405; 3,503,869; 2,899,365 and 3,297,562.

Free fall oil shale hydrogasification is taught by U.S. Pat. No. 3,421,868. The '868 patent teaches production of relatively high Btu gas from oil shale by passing freely falling oil shale in contact with hydrogen which is passed either cocurrent with or countercurrent to the free falling shale. The '868 patent teaches the desirability of low hydrogen to shale ratios and flow rates of hydrogen gas much lower than flow rates of shale solids, resulting in much longer gas residence time than solids residence time within the reactor. The process of the '868 patent does not require heat input to the reaction zone. The '868 patent teaches that the disclosed free falling shale process substantially reduces decomposition of mineral carbonates while providing substantially the same gaseous yield as previous moving bed processes.

U.S. Pat. No. 4,012,311 teaches a process for high yield of coal tars by contacting coal in a series of free fall reaction zones with a cocurrent flow of hydrogen followed by quick quenching and removal of coal tar prior to entry to the next reaction zone. The '311 patent teaches low hydrogen to coal ratios and the importance of very rapid heat-up, short residence time, and quenching.

SUMMARY OF THE INVENTION

This invention relates to a process for increased production of liquid and gaseous hydrocarbons from solid organic carbonaceous materials of the type having a sufficiently high density, such as oil shale, coal, peat and biomass, to free fall in a lean solids stream countercurrent to a hydrogen-containing gas stream. The liquid and gaseous hydrocarbon products formed according to the process of this invention are especially suitable for fuels. The process of this invention involves the solid organic carbonaceous material passing in free fall countercurrent flow relation to hydrogen-containing gas sequentially through a preheat and pretreatment zone, a reaction zone, and a hydrogen-containing gas preheat zone. A high hydrogen to organic carbon ratio of about 10 to about 30 Standard Cubic Feet of hydrogen per pound of carbonaceous material is maintained in the reaction zone, providing a lean solids stream. Further, short gas residence times, as compared to solid residence times, are provided by the hydrogen-containing gas moving countercurrently to the organic carbonaceous solids at a higher flow rate than the solid material. A solids residence time in the reaction zone of about 20 to about 200 seconds at temperatures of about 800° to about 2000° F. predominately forms the desired liquid and gaseous hydrocarbon products which are removed from the upper portion of the vertical reactor vessel and the spent carbonaceous material is removed from the lower portion of the reactor vessel. For preferential liquid production, the reaction zone temperatures are about 800° to about 1300° F. and for preferential gas production about 1400° to about 2000° F.

The process of this invention in one embodiment provides that the solid organic carbonaceous material and the hydrogen-containing gas is introduced at about ambient temperatures. The problems of liquid condensation and clogging previously encountered in moving bed reaction processes, is considerably reduced or eliminated in the process of this invention, thereby providing a higher useful yield of the more desired saturated liquid hydrocarbon products. Variation of process conditions within specified limits provides for utilization of a wide variety of organic carbonaceous containing feed solids.

It is an object of this invention to provide a process for production of liquid and gaseous hydrocarbons from solid carbonaceous materials having a sufficiently high density to free fall in a lean solids stream countercurrent to a hydrogen-containing gas stream by passing the carbonaceous material in free fall countercurrent flow relation to hydrogen-containing gas in a single vertical reactor.

It is another object of this invention to provide a process for production of liquid hydrocarbon products from heavy organic carbonaceous materials in a free fall countercurrent flow reactor free from clogging problems experienced in prior moving bed reactors.

It is yet another object of this invention to provide a process for production of liquid fuels from carbonaceous materials in which prior problems of liquid condensation in moving bed reactors is greatly reduced or eliminated.

These and other objects and advantages will become apparent upon reading the detailed description of preferred embodiments with reference, to the drawings.

BRIEF DESCRIPTION OF THE DRAWINGS

FIG. 1 is a cross-sectional view of a reactor vessel according to one embodiment of this invention and suitable for carrying out the process of this invention; and FIG. 2 is a cross-sectional view of the upper portion of a reactor of another embodiment for use in the process of this invention.

DESCRIPTION OF THE PREFERRED EMBODIMENTS

Carbonaceous materials useful as feed materials in this invention are solid organic carbonaceous materials having sufficiently high density to cause solid particles of a size providing reasonably high reactive surface area to fall in a lean solids stream countercurrent to a hydrogen-containing gas stream. The particle size may vary over quite wide ranges dependent upon the density of the solids. Suitable particle sizes are generally about −10 to about +200 U.S. Sieve. Suitable solid organic carbonaceous material is selected from the group consisting of oil shale, coal, peat and biomass.

Oil shales of the Eocene period generally found in the, western United States, particularly the northwestern area of Colorado and in the adjoining areas of Utah and Wyoming are suitable for use in this invention. These oil shales have an organic carbon to hydrogen weight ratio typically of less than 8/1 and usually of 7/1 to 8/1 and Modified Fischer Assays in the order of 25 gallons per ton or more. Oil shales have large quantities of "Black Shale" from deposits such as Devonian and Mississippian, generally found in the eastern portion of the United States are especially suitable for use in this invention. These oil shales have been found to have organic carbon to hydrogen weight ratios typically in the order of 10/1 up to about 13/1 and Modified Fischer Assays of less than 10 gallons of oil per ton and frequently as low as less than 5 gallons of oil per ton. The Modified Fischer Assays have been found to not represent the organic carbon actually present in the "eastern" type shale having the higher organic carbon to hydrogen weight ratios. Further, the inorganic carbon present in the "eastern" type oil shales is lower than that of the "western" type oil shales by a factor of greater than 10 and up to 30 to 40. The following table gives estimated compositions of both the organic and inorganic portions of a typical "eastern" and "western" oil shale.

TABLE I

| | Source of Oil Shale | |
|---|---|---|
| | Clark County, Ind. (Eastern) | Colorado (Western) |
| | Weight Percent | |
| Organic | | |
| Carbon | 13.7 | 13.6 |
| Hydrogen | 1.2 | 1.9 |
| Sulfur | 0.3 | 0.3 |
| Nitrogen | 0.4 | 0.5 |
| Oxygen | 1.0 | 1.7 |
| Carbon/Hydrogen | 11.4 | 7.2 |
| Inorganic | | |

TABLE I-continued

| | Source of Oil Shale | |
|---|---|---|
| | Clark County, Ind. (Eastern) | Colorado (Western) |
| | Weight Percent | |
| Carbon Dioxide | 0.5 | 15.9 |
| Water | 4.0 | 1.8 |
| Sulfur | 4.4 | 0.2 |
| Ash | 78.3 | 66.8 |
| Modified Fischer Assay | | |
| gal/ton | 10 | 30 |

The excess of the totals over 100 percent is thought to be due to weight gain by oxidation of metals in the mineral component during ashing. It is readily observed from Table I that while the organic carbon content of the two oil shales is almost identical, the Modified Fischer Assay varies by a factor of 3. Oil shale having the properties set forth above as typical of "eastern" shale are particularly preferred for use in the process of this invention. Suitable coal for use in the process of this invention includes anthracite, bituminous and lignite. Peat suitable for use in this invention includes new peat and old peat.

Biomass materials suitable for use in this invention include heavy biomass materials such as organic solid sanitary and agricultural wastes and woods.

Suitable sizes for introduction of the solid organic carbonaceous material are about −10 to about +200 U.S. Sieve, about −55 to +200 U.S. Sieve being preferred. The size of the particles is dependent upon the density of the particle so as to provide desired free fall velocity against the countercurrent gas flow with a net velocity as set forth further herein. The solid organic carbonaceous materials useful as feed stock in this invention generally have a density of about 50 to about 200 pounds per cubic foot.

Referring to FIG. 1, the solid organic carbonaceous material may be pretreated in any desired fashion, such as reduction of moisture content, and provided to solids storage hopper 21 which, together with solids introduction conduit 22 and solids introduction feed means 23, make up solids feeding means 20. Any suitable solids feeding means as known to the art may be used. The feed solids are introduced to reactor 10 through vessel top bell 14 and pass over solids distribution baffles 24 to provide even distribution of the introduced solids across the area of the reactor. The solids pass downwardly by gravity and pass sequentially through solids preheat and pretreatment zone I, reaction zone II, heat addition zone III and hydrogen containing gas preheat zone IV. Heat addition zone III is provided between hydrogen-containing gas preheat zone IV and reaction zone II to provide the necessary addition of heat to maintain the reaction zone II at temperatures of about 800° to about 2000° F. The spent solids leave the reactor by spent solids discharge conduit 19 through reactor vessel bottom 16.

Hydrogen-containing gas passes upward through reactor 10 countercurrent to the downward passage of the solid organic carbonaceous material. Hydrogen-containing gas at or near ambient temperature conditions may be introduced to the lower portion of the reactor vessel through gas introduction conduit 31 controlled by valve $V_1$ and pass upwardly through gas distributor plate 32 and through hydrogen-containing gas preheat zone IV wherein the free falling solid particles transfer heat to the countercurrent flowing gas stream. The hydrogen-containing gas stream is further heated in heat addition zone III which may be considered, and is meant to be considered for the purpose of this disclosure and claims, as the lower portion of reaction zone II since further reaction may take place in zone III. Hot hydrogen-containing gas or hot non-reactive solids may be introduced through hot gas/solids conduit 44 controlled by valve $V_4$. Any suitable means may be used to distribute the hot gas or hot solids generally uniformly across the reactor cross section. The amount of heat necessary to add in heat addition zone III is that amount sufficient to maintain the reaction zone II at desired temperatures of about 800° to about 2000° F. In preferred embodiments the temperatures in reaction zone II are maintained at about 800° to about 1200° F. for the production of liquids and at about 1400° to about 2000° F. for the production of gases. In one embodiment of this invention, the spent particles removed through discharge conduit 19, particularly when coal or peat is used as feed solids, may be combusted in a separate combustion process to heat the hydrogen-containing gas or non-reactive solids for introduction through conduit 44. It will be apparent that the amount of hydrogen-containing gas introduced through each of conduits 31 and 44 may be advantageously adjusted to provide the desired heat to reaction zone II. Thermal energy may also be provided to heat addition zone III by addition of combustible material through conduit 41 controlled by valve $V_3$ and mixing with oxygen-containing gas, such as air, introduced through conduit 42 controlled by valve $V_2$ in an amount sufficient for internal combustion within heat addition zone III to provide the desired temperatures in reaction zone II. Hydrogen may be combusted in heat addition zone II and such combustion may be controlled by control of the addition of oxygen.

The upwardly flowing hydrogen-containing gas stream entering reaction zone II is in an amount of about 10 to about 30 Standard Cubic Feet of hydrogen per pound of raw carbonaceous material in countercurrent flow thereto. It is preferred that the hydrogen-containing gas is introduced to the reaction zone in an amount of about 15 to about 25 Standard Cubic Feet of hydrogen per pound of the countercurrent flowing carbonaceous material. The solid carbonaceous material moves downwardly through the reaction zone at about 0.5 to about 2 feet per second, preferably about 1 to about 1.5 feet per second, while the hydrogen-containing gas moves counter-currently upward at a higher flow rate and about 1 to about 5 feet per second, preferably about 2 to about 4 feet per second, providing solids residence time in the reaction zone of about 20 to about 400 seconds. In a preferred embodiment, the solids residence time in the reaction zone is about 50 to about 200 seconds.

The upwardly flowing hydrogen-containing gas stream leaving reaction zone II passes upwardly through preheat and pretreatment zone I. In the solids preheat and pretreatment zone, thermal transfer between the hydrogen-containing gas and carbonaceous solids takes place cooling the gas and heating the solids. The hydrogen-rich gas pretreats the organic carbonaceous material by contact with it in such a manner as to improve obtention of desired substantially saturated liquid and gaseous hydrocarbon products in the reaction zone. The upwardly moving hydrogen-containing gas stream also carries the gaseous and vaporized liquid products from hydroconversion of the solid organic carbonaceous material in the reaction zone. The height of the solids preheat and pretreatment zone may be sufficient to allow substantial thermal exchange to take place which heats the free falling solids to near the desired temperature of the reaction zone and for pretreatment of solid organic carbonaceous material to render it more suitable for conversion of the organic carbonaceous component to liquid and gaseous hydrocarbon products in the reaction zone. This is practical due to the lean solids phase which will continue to flow uniformly even in the presence of condensation and refluxing of liquids on the solid particles. The lean phase solids virtually eliminates any problem of clogging due to condensation as encountered by the prior art with moving bed reaction systems. The gas stream passes upwardly from the solids preheat and pretreatment zone to a solids/gas separator means 33 located in upper zone 12 of the reactor. Solids/gas separator means may be conventionally used cyclones as are well known to the art or any other means for separation of entrained solids from the product gas. The solids/gas separator means is preferably located within the reactor vessel so that the solids may be returned directly to the solids preheat and pretreatment zone for recycle. Hydrogen containing gas with entrained product vapor and gases passes from the reaction system through product conduit 34.

The product stream comprises hydrocarbon liquids and low molecular weight paraffinic gases. The desired hydrocarbon liquids produced by the process of this invention are especially suited for further processing, such as production of naphtha, gasoline, kerosene, jet fuel, diesel oil and light fuel oils, and other low boiling distillate oils as well as for conversion to high methane content pipeline quality gas. The desired low molecular weight paraffinic gas products include molecules of 4 and less carbon atoms, namely, methane, ethane, propane butane and isobutane. When liquid product is desired, the process may be adjusted as described above so that less than about 20 percent of the organic carbonaceous material is converted to the gas form.

The terminology "hydrogen-containing gas" throughout this description and claims, means gases having sufficient hydrogen partial pressure to effect high organic carbon hydroconversion from the organic carbonaceous feed material. Such hydrogen-containing gases may be obtained by a number of processes well known in the chemical process industry. It is preferred to use hydrogen containing gas having a partial pressure of hydrogen greater than about 100 psia. The upper operating pressures are limited only by equipment and economic considerations. Higher hydrogen partial pressures allow higher reaction rates and thus smaller reactors. Total operating pressures throughout the process system are usually substantially the same. Normally, the process of this invention may be carried out at total pressures of about 40 to 1500 psia, preferably about 500 to 1000 psia.

A particularly well suited reactor for carrying out the process of this invention is shown in FIG. 1. Vertical reactor vessel 10 has substantially vertical walls 11 through its central portion, the walls extending outwardly shown as expanded vessel walls 12 forming an expanded volume in the upper portion of the reactor. A bell-shaped reactor top 14 has depending walls 17 substantially in line with the reactor vessel walls 11 and extend downwardly in the expanded volume having their bottom ends spaced from reactor walls 11 forming an annular solids/gas separation zone between depending walls 17 and expanded vessel walls 12. Depending walls 17 define a solids distribution zone having solids distribution baffles 24 capable of distributing the feed solids substantially evenly across the area of the reactor vessel. Solids feed means 20 introduces feed solids into the upper portion of the solids distribution zone and may be any suitable feed means capable of supplying solids to the pressurized vessel. Solids/gas separator means 33 are located within the annular solids/gas separation zone and may feed the solids directly back to the straight wall portion of the reactor vessel. Product conduit 34 is in communication with the gas exit of the solids/gas separator means 33 and conveys the products from the reactor. In the lower portion of the reactor, gas distribution means 32 is capable of distributing passing gas across the cross section of the reactor vessel. Gas introduction and supply means 31 allows the entry of hydrogen-containing gas to the portion of the reactor vessel below gas distribution means 32. While with some organic carbonaceous feed materials the ash will be carried out with the product stream, spent solids discharge conduit 19 with valve 5 is provided in case of spent solids which are too large to be removed with the product gas. The process of this invention requires addition of heat. A particularly suitable means for introduction of heat to a heat addition zone in the lower portion the reaction zone is shown in FIG. 1 wherein upwardly extending expanded vessel wall 13 and downwardly extending vessel wall 15 form an annular volume around the heat addition zone to provide for introduction of hot particulates, hot gases or combustible materials for internal combustion within the heat addition zone.

FIG. 2 shows another preferred embodiment for solids introduction and distribution substantially evenly across the area of the reactor vessel. Fluidized bed support 25 extends across the lower portion of depending walls 17 and a plurality of overflow tubes 27 extend from the height of the fluidized bed 26 downwardly through support plate 25 distributing solids substantially evenly across the area defined by reactor vessel walls 11. It is preferred that the lower ends of overflow tubes 27 have baffles 29 to prevent entry of product vapor.

The apparatus of this invention may be constructed of materials apparent to those skilled in the art upon reading this disclosure and are principally dependent upon desired operating temperatures and pressures as well as overall reactor size.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A process for production of liquid and gaseous hydrocarbon products comprising:
    introducing solid organic carbonaceous material into the upper portion of a vertical reactor vessel;
    introducing hydrogen containing gas into the lower portion of said reactor vessel;
    passing said carbonaceous material of a size and sufficiently high density to free fall in a lean solids stream in countercurrent flow relation to said hydrogen containing gas from said upper portion to said lower portion and passing said hydrogen containing gas from said lower portion to said upper portion, said carbonaceous material passing sequentially and said hydrogen containing gas passing in reverse sequence through a solids preheat and pretreatment zone, a reaction zone, a heat addition zone, and a hydrogen containing gas preheat zone, introducing hydrogen containing gas to said reaction zone in an amount of about 10 to about 30 Standard Cubic Feet hydrogen per pound of said carbonaceous material, said solid carbonaceous material moving downwardly about 0.5 to about 2 feet per second and said hydrogen containing gas moving upwardly at a higher flow rate than said solid material is moving downwardly and about 1 to about 5 feet per second providing solids residence time in said reaction zone of about 20 to about 400 seconds at temperatures of about 800° to about 2000° F. forming predominantly said liquid and gaseous hydrocarbon products, the amount of heat added in said heat addition zone being sufficient to maintain said temperatures in said reaction zone; and
    removing said products and excess hydrogen containing gas from the upper portion and spent carbonaceous material from the lower portion of said reactor vessel.

2. The process of claim 1 wherein said solid organic carbonaceous material is introduced at about ambient temperature.

3. The process of claim 1 wherein said hydrogen containing gas is introduced at about ambient temperature.

4. The process of claim 1 wherein said temperatures are about 800° to about 1200° F. and said products are predominantly liquid hydrocarbons.

5. The process of claim 1 wherein said temperatures are about 1400° to about 2000° F. and said products are predominantly gaseous hydrocarbons.

6. The process of claim 5 wherein said gaseous hydrocarbons comprise predominantly paraffinic hydrocarbons selected from the group consisting of methane, ethane, propane, butane and isobutane.

7. The process of claim 1 wherein said hydrogen containing gas is introduced to said reaction zone in an amount of about 15 to about 25 Standard Cubic Feet hydrogen per pound of said carbonaceous material.

8. The process of claim 1 wherein said carbonaceous material moves about 1 to about 1.5 feet per second.

9. The process of claim 1 wherein said hydrogen containing gas moves about 2 to about 4 feet per second.

10. The process of claim 1 wherein said solids residence time in said reaction zone is about 50 to about 200 seconds.

11. The process of claim 1 wherein said solid organic carbonaceous material is selected from the group consisting of oil shale, coal, peat and biomass.

12. The process of claim 11 wherein said solid organic carbonaceous material is oil shale.

13. The process of claim 12 wherein said oil shale has an organic carbon to hydrogen weight ratio of about 9 to about 14 and a Modified Fischer Assay of less than about 9 gallons of oil per ton.

14. The process of claim 12 wherein said oil shale has a Modified Fischer Assay corresponding to less than half the organic carbon present.

15. The process of claim 1 wherein said solid organic carbonaceous material is introduced into the upper portion of said reactor vessel by passage over a plurality of solids distributor baffles to distribute said solids throughout the cross-sectional area of said reactor.

16. The process of claim 1 wherein said solid organic carbonaceous material is introduced into the upper portion of said reactor by introduction into a fluidized bed maintained in a fluidized state by passage of a portion of said products and excess hydrogen containing gas therethrough, the upper portion of said fluidized bed entering a plurality of overflow tubes to distribute said solids throughout the cross-sectional area of said reactor.

17. The process of claim 1 wherein said solid organic carbonaceous material is of a size of about −10 to about +200 U.S. Sieve.

* * * * *